(12) United States Patent
Doell et al.

(10) Patent No.: US 10,857,342 B2
(45) Date of Patent: Dec. 8, 2020

(54) MEDICAL TORSION TOOL

(71) Applicant: Ingenyewity Inc., Markham (CA)

(72) Inventors: Michael Doell, Markham (CA); Maria Plummer, Markham (CA); Corinna Ienna, Ottawa (CA)

(73) Assignee: Ingenyewity Inc., Markham (CA)

( * ) Notice: Subject to any disclaimer, the term of this patent is extended or adjusted under 35 U.S.C. 154(b) by 599 days.

(21) Appl. No.: 14/990,184

(22) Filed: Jan. 7, 2016

(65) Prior Publication Data
US 2017/0157358 A1    Jun. 8, 2017

(30) Foreign Application Priority Data
Dec. 7, 2015 (CA) ...................... 2914298

(51) Int. Cl.
*A61M 39/08* (2006.01)
*A61M 25/01* (2006.01)

(52) U.S. Cl.
CPC ........... *A61M 39/08* (2013.01); *A61M 25/013* (2013.01); *A61M 2039/087* (2013.01)

(58) Field of Classification Search
CPC ............ A61M 39/08; A61M 25/01–13; A61M 39/28–39/288; A61M 39/10–2039/1016; B25B 9/02; B25B 27/00
USPC .............. 606/1, 120; 251/9–10; 24/455–571; 81/418–423, 424.5–427
See application file for complete search history.

(56) References Cited

U.S. PATENT DOCUMENTS

| | | | |
|---|---|---|---|
| 3,061,263 A | | 10/1962 | Butler |
| 3,896,527 A | * | 7/1975 | Miller ............ A44B 99/00 16/DIG. 13 |
| 4,091,815 A | * | 5/1978 | Larsen ............ A61B 17/122 24/132 WL |
| 4,346,869 A | | 8/1982 | MacNeill |
| 4,434,963 A | | 3/1984 | Russell |
| 4,449,530 A | * | 5/1984 | Bendel ............ A61B 17/122 606/158 |

(Continued)

FOREIGN PATENT DOCUMENTS

| | | |
|---|---|---|
| CN | 201006148 Y | 1/2008 |
| CN | 203342171 U | 12/2013 |

(Continued)

OTHER PUBLICATIONS

Evriholder Easy Twist Jar Opener Lid Remover—Assorted Color; Date first listed on Amazon Nov. 1, 2000; Amazon; https://www.amazon.com/Evriholder-Easy-Twist-Opener-Remover/dp/B000O87VUA (Year: 2000).*

(Continued)

*Primary Examiner* — Jonathan T Kuo
(74) *Attorney, Agent, or Firm* — Banner & Witcoff, Ltd.

(57) ABSTRACT

Provided is a medical tool for disconnection of a medical tubing connection comprising a resilient body forming a pair of open biased opposing jaws joined at a connected end; and gripping elements on an inside surface of each opposing jaws near the connected end to grip the medical tubing when the opposing jaws are moved together, to allow disconnection of the medical tubing connection. Also provided is a use of the medical tool for disconnecting medical tubing connection and a method for disconnecting medical tubing connection using the medical tool.

12 Claims, 5 Drawing Sheets

(56) References Cited

U.S. PATENT DOCUMENTS

| | | | |
|---|---|---|---|
| 4,509,784 A * | 4/1985 | Vollers | B67B 7/18 294/99.1 |
| 4,671,282 A * | 6/1987 | Tretbar | A61B 17/12 24/703.1 |
| 5,006,830 A * | 4/1991 | Merritt | A61B 17/12 283/75 |
| 5,401,256 A | 3/1995 | Stone et al. | |
| 5,817,116 A | 10/1998 | Takahashi et al. | |
| 6,195,862 B1 | 3/2001 | Chang | |
| D524,612 S * | 7/2006 | Wakasugi | D8/18 |
| 7,918,002 B2 | 4/2011 | Kissel | |
| 8,337,411 B2 * | 12/2012 | Nishtala | A61B 5/205 600/561 |
| D781,676 S * | 3/2017 | Stauffacher | D8/39 |
| 2003/0074009 A1* | 4/2003 | Ramsey | A61B 17/122 606/120 |
| 2004/0255436 A1 | 12/2004 | Fujii | |
| 2007/0112376 A1 | 5/2007 | Propp | |
| 2009/0221933 A1* | 9/2009 | Nishtala | A61B 5/205 600/561 |
| 2010/0280459 A1 | 11/2010 | Werner | |
| 2010/0294271 A1 | 11/2010 | Pittaway et al. | |
| 2014/0259548 A1 | 9/2014 | Perullo | |

FOREIGN PATENT DOCUMENTS

| | | |
|---|---|---|
| CN | 104096312 A | 10/2014 |
| CN | 203971133 U | 12/2014 |
| JP | 2015073673 A | 4/2015 |
| WO | 0077428 A2 | 12/2000 |
| WO | 2011103302 A2 | 8/2011 |
| WO | 2013004322 A1 | 1/2013 |
| WO | 2013177537 A1 | 11/2013 |
| WO | 2014036325 A2 | 3/2014 |

OTHER PUBLICATIONS

GE Healthcare Life Sciences; Vacuum filtration: How to set up with Büchner flask and funnel; Published Jun. 15, 2015 on YouTube; https://www.youtube.corn/watch?tirne_continue=89&v=Kj5YF2zPBbE (Year: 2015).*
http://medegrip.com/luer.html.
http://www.oxygenconcentratorstore.com/o2-talon.
http://www.pahsco.com.tw/product_detail-157.

* cited by examiner

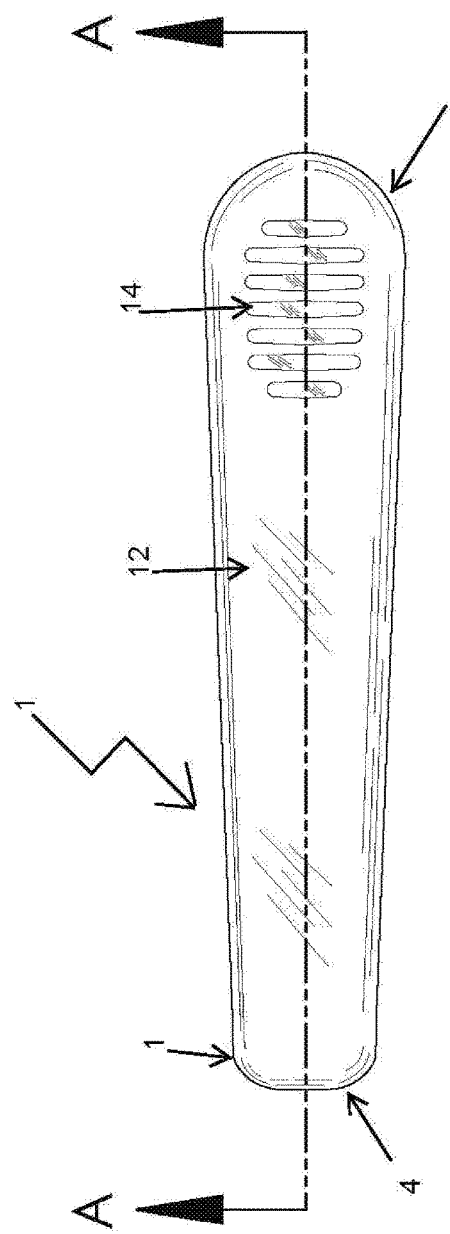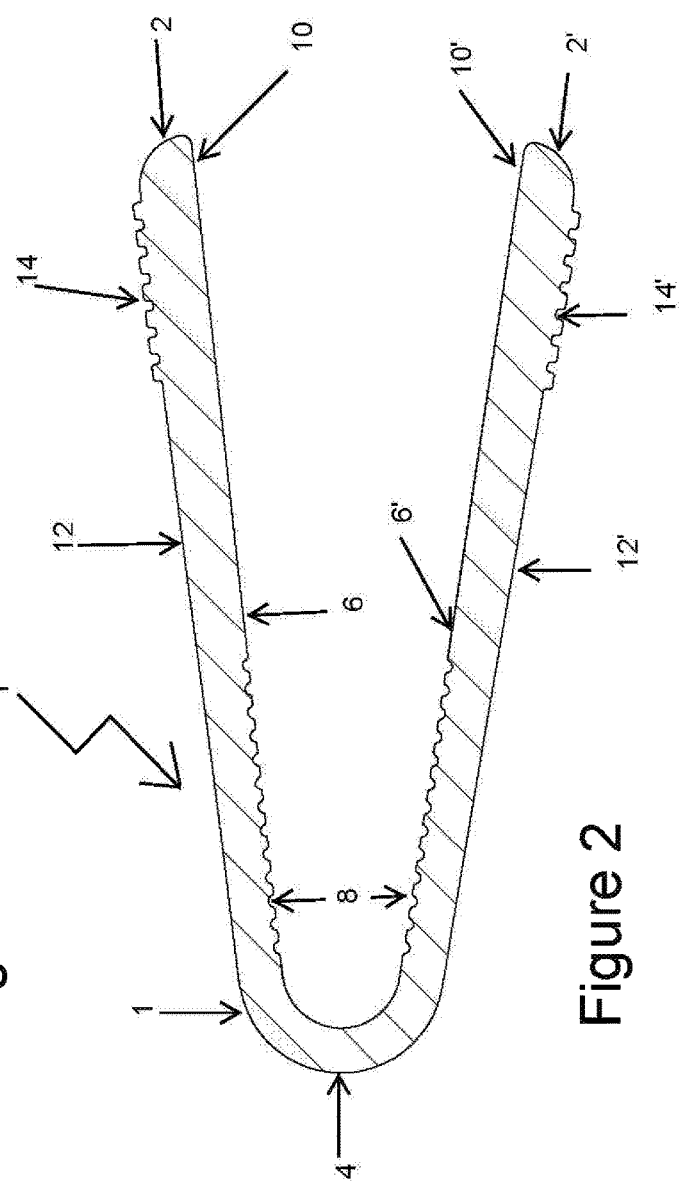

MEDICAL TORSION TOOL

FIELD OF THE DISCLOSURE

The described embodiments are directed to the medical field, in particular to medical tools for assisting health professionals or other caregivers in disconnecting medical tubing from various connections.

BACKGROUND TO THE INVENTION

In the medical field, there exists a wide variety of medical tubing and different connection types. The various medical tubing connections need to be handled safely and frequently; and encountering a tight connection represents a major problem. Health professionals or other caregivers are faced with wasted time, damaged tubing, hazardous spill, or the like, when trying to disconnect tight connections or connections they are physically unable to untighten. There is a need to provide a safe and universal tool that will quickly and easily disconnect a tight connection.

Existing devices for assisting in disconnection of various connections are provided, for example, in U.S. Pat. No. 7,918,002 or 6,195,862. U.S. Pat. No. 7,918,002 discloses a disconnect tool for pneumatic and hydraulic systems in automotive, marine and industrial applications for disconnecting a tubing end that is inserted within a collet of a fitting comprising a first plate member, a second plate member and bias member. The first plate member has a first front portion, a first rear portion and a first middle portion. The first plate member further has a channel disposed within the first middle portion. The second plate member has a second front portion, a second rear portion and a second middle portion. The second plate member also has a second channel disposed within the second middle portion. The bias member connects the first plate member and the second plate member such that the bias member spaces the first plate member to attach to the fitting and spaces the second plate member to contact an outer collet surface of the collet wherein the first channel is configured to engage an engagement surface of the fitting and the second channel is configured to contact the outer collet surface in order to force the outer collet surface against the fitting to release the tubing end. This tool only permits disconnection of tubing connections with sizes and shapes that fit in the channels of the device. It does not grip the tubing but is rather inserted around the connection. Also, it does not allow torsion for improved strength and leverage.

U.S. Pat. No. 6,195,862 discloses a tool specifically designed for mechanical applications for disconnecting flexible tubing telescoping around cylindrical connection nipples jutting from planer surfaces in narrow confined spaces. The tool includes cooperating semi-annular 'clamshell' heads located at the distal ends of two pivotally coupled shank arms oriented, upon closing, to form an annular tool body that has a longitudinal axis extending at an acute angle out of the engagement/working tip of the tool body relative to the plane of the pivoting coupled shank arms. This device is not adaptable to any size of tubing or any type of connection; again only a limited selection would fit in the fixed shape heads.

Health professionals generally use common tools in hand, for example hemostats or metal pliers, when trying to disconnect tight medical tubing connections. These methods can potentially damage the medical tubing, and therefore cause hazardous spills such as chemotherapy agents, radioactive substances, blood or blood products. Patients are also at risk of infection if the medical tubing is damaged. In extreme circumstances, such as ICU and emergency environment, it can represent a life-threatening situation. Most of these common tools are not safe and therefore not approved in health care facilities.

The existing devices and solutions do not provide adaptability to various types and sizes of tubing and connections, while being safe, light, strong and easy to use. There is a need to provide a medical tool to overcome these disadvantages.

SUMMARY

Certain exemplary embodiments provide a medical tool for disconnection of a medical tubing connection, the medical tool comprising: a) a resilient body forming a pair of open biased opposing jaws joined at a connected end; and b) gripping elements on an inside surface of each opposing jaws near the connected end to grip the medical tubing when the opposing jaws are moved together, to allow disconnection of the medical tubing connection.

Other exemplary embodiments provide use of a medical tool for disconnecting a medical tubing connection, the medical tool comprising: a) a resilient body forming a pair of open biased opposing jaws joined at a connected end; and b) gripping elements on an inside surface of each opposing jaws near the connected end to grip the medical tubing when the opposing jaws are moved together to allow disconnection of the medical tubing connection.

Yet other exemplary embodiments provide a method for disconnecting a medical tubing connection with a medical tool, the method comprising: a) providing a medical tool; wherein the medical tool comprises i) a resilient body forming a pair of open biased opposing jaws joined at a connected end; and ii) gripping elements on an inside surface of each opposing jaws near the connected end; b) inserting a medical tubing in between the opposing jaws near the connected end; c) moving the opposing jaws towards each other to grip the medical tubing; d) disconnecting the medical tubing connection.

BRIEF DESCRIPTION OF THE DRAWINGS

Various embodiments will now be described in further detail with reference to the following drawings, in which:

FIG. 1 is a top view of an embodiment of a medical tool;
FIG. 2 is a cross-section view along axis A of FIG. 1.

DEFINITIONS

Figure 3:
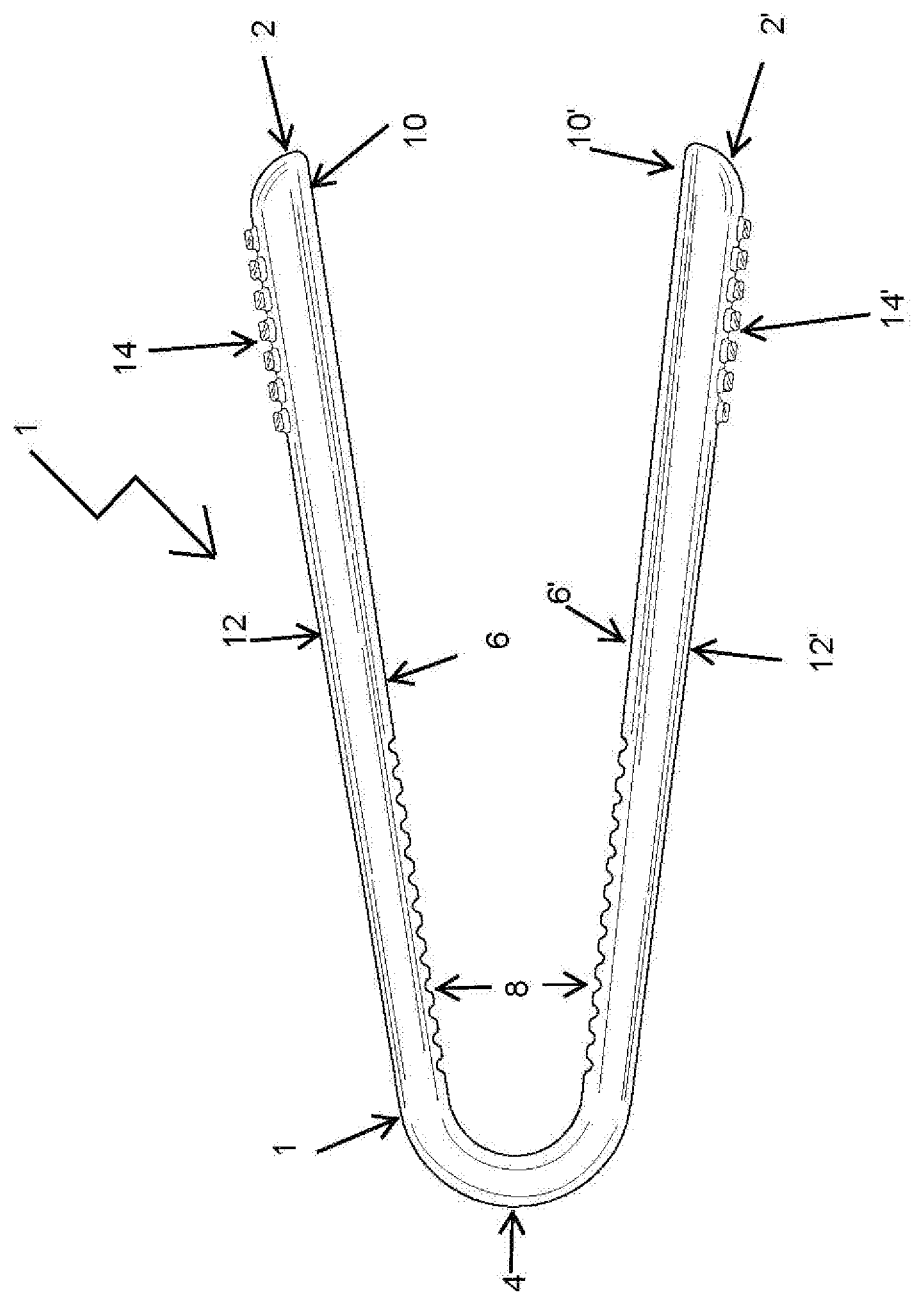
FIG. 3 is a side view of FIG. 1.
Figure 5:
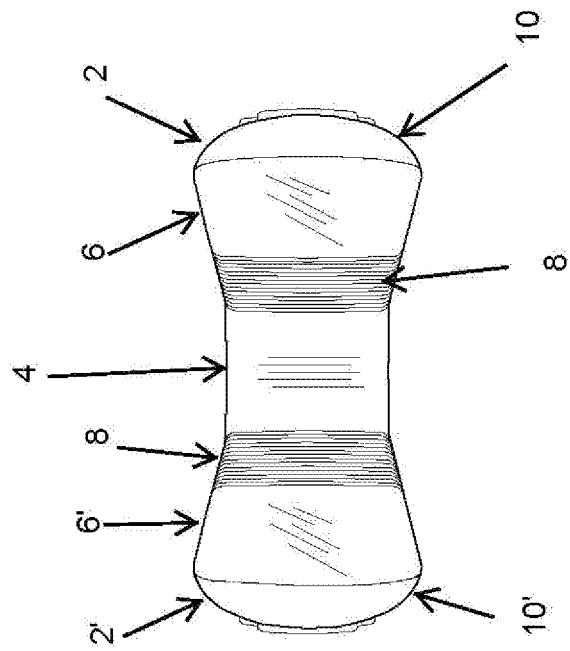
FIG. 5 is a view from the opposite end of FIG. 1.
Figure 4:
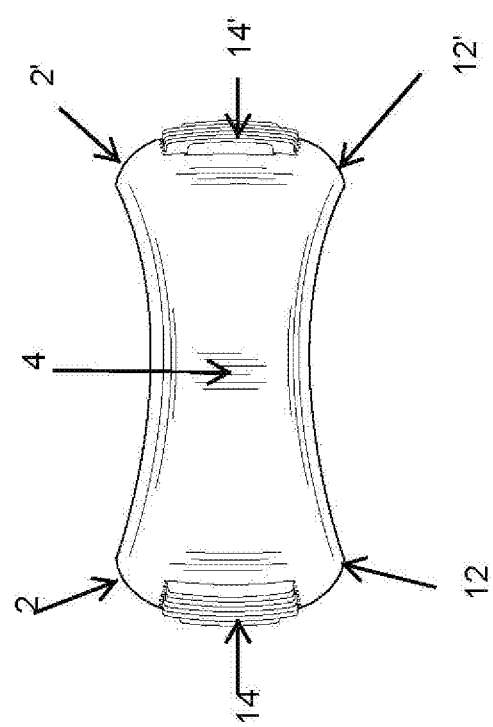
FIG. 4 is a view from the connected end of FIG. 1.
Figure 6:
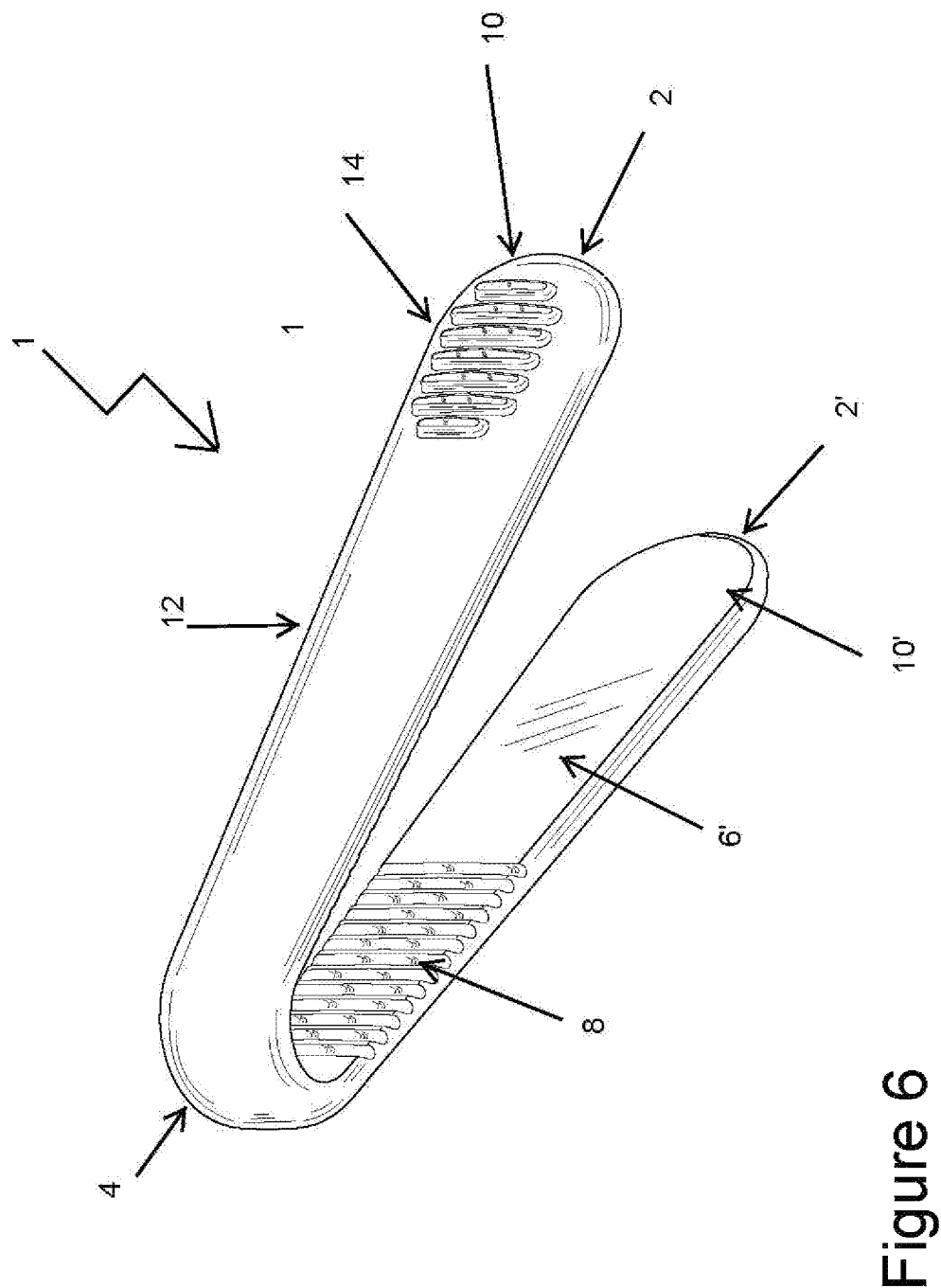
FIG. 6 is a perspective view of FIG. 1.

"Medical tubing" used herein generally refers to any hollow tubing that is used in the medical field such as intravenous tubing, drainage collections device, chest tube, peritoneal catheters, gastrostomy tubes, urinary tubes, ileal conduits, or the like. The fluid circulating within such tubing can be either flowing into the patient or out of the patient.

"Connection" used herein generally refers to any kind of medically accepted attachment of medical tubing to other pieces of medical equipment. For example an intravenous tubing can be connected to a patient's access line for administration of fluids or medications.

"Resilient" used herein generally refers to an object able to recoil or spring back into shape after bending, stretching, or being compressed.

"Bias" used herein generally refers to a forced direction of movement between two points, making the object move in a particular direction.

"Transversal" used herein generally refers to a line or a plane that intersects a system of other lines.

"Longitudinal" used herein generally refers to a line or a plane extending in the direction of the length of an object; lengthwise. or extending along the long axis of the object.

"Inwardly projecting" used herein generally refers to a part extending beyond; protruding toward the inside.

"Ribs" used herein generally refers to long raised pieces across a surface or through a structure, which typically serve to support or strengthen.

"Concave" used herein generally refers to an outline or surface that curves inward like the interior of a circle or sphere.

"Rubber" used herein generally refers to any of numerous synthetic elastic materials of varying chemical composition with properties similar to those of natural rubber; an elastomer.

DETAILED DESCRIPTION OF THE INVENTION

Patients in different health care environments, either at home, in a hospital, a clinic or the like, are often connected to medical tubing for various health reasons, such as intravenous lines, blood administration or collection lines, lines for blood product like platelets, plasma, albumin, etc., dialysis lines, apheresis lines, filtered lines, various types of drainage collection devices (ie. Hemovacs), chest tubes, peritoneal catheters, nasogastric tubes, gastrostomy tubes, urinary tubes, ileal conduits etc. For example, central or peripheral intravenous lines inserted in a patient can be connected to an end cap, a normal saline lock, extension tubing, an intensive care unit (ICU) medical bar, a medication pump, or the like. When caring for patients, health professionals, or any other caregivers, or even the patient himself, often need to disconnect medical tubing connections, for example when a treatment is completed, to change tubing or end caps on a regular basis to prevent infection, or the like. The connections can be extremely tight and difficult to disconnect or remove. When encountering such tight connections, frustration, delay in medical procedures, etc, can result for the health professional and other caregivers, but also generates stress and anxiety for the patient witnessing the professional struggling. Also, common methods to solve the problem can likely damage the medical tubing, presenting a risk of infection for the patient, spillage of valuable and/or hazardous material, etc.

As shown in FIGS. 1 to 6, a medical tool 1 of various embodiments may comprise a body forming a pair of opposing jaws 2, 2' joined at a connected end 4. The body may be resilient and deformable to allow the jaws 2, 2' to move between a biased open position and a gripping position. The inside surface 6, 6' of each jaw 2, 2' may be provided with gripping elements 8, near the connected end 4 to facilitate gripping of the medical tubing or connection. The gripping elements 8 on each jaw 2 or 2' are preferably transversal and inwardly projecting ribs. The gripping elements 8 may extend to only a small portion of the inner surface 6, 6' at the connected end 4, for example 20%, 30%, or 50% of the surface or the gripping elements 8 may extend to all the inner surface 6, 6' up to the opposite end 10, 10' (not shown).

When the medical tool 1 is in the open position, a connected medical tubing, or the connection itself may be inserted near the connected end 4 of the medical tool 1, in between the opposing jaws 2, 2'. Pressure may be applied at the opposite end 10, 10' to move together the jaws 2, 2' towards the gripping position to grip the medical tubing or connection. In one embodiment, at least one jaw 2 or 2' may be provided on the outside surface 12, 12' at end 10, 10' with friction elements 14, 14' for better gripping of the medical tool 1 by a user. Preferably, both jaws 2, 2' are provided with friction elements 14, 14'. The friction elements 14, 14' may be for example transversal or longitudinal outwardly projecting ribs, concave or indented portions, or the like. Upon pressure to move the jaws 2, 2' together towards the gripping position, the medical tubing or connection is gripped between the gripping elements 8 and the user can twist or pull to disconnect a tight connection. The medical tool 1 described may therefore provide leverage to disconnect tight medical tubing connections.

It can be understand that various types and sizes of tubing and connections can be inserted in the medical tool 1, provided that it fits in between the opposing jaws 2, 2' in the open position. Should a smaller tubing or connection be too small to be gripped properly at the connected end 4, the small tubing may be placed in between the jaws 2, 2' near the open end 10, 10' and the medical tool 1 may be used like tweezers. Therefore, the medical tool 1 described may provide adaptability and versatility for various uses and circumstances.

The body of the medical tool 1 is typically made of plastic material. Therefore, the medical tool 1 may be durable and light for portability and easiness of use. For example the medical tool 1 described can be carried in pockets of a health professional's uniform, and be readily available and quickly use when needed. The material may be durable and not damageable to medical tubing, such as polypropylene, rubber, etc. Although the medical tool described is adaptable to most typical medical tubing, it may be appreciated that the medical tool can be manufactured in various sizes for different intended purposes involving different sizes or types of medical tubing.

In one embodiment, the opposing jaws 2, 2' are molded together. The resiliency of the molded material may provide the medical tool 1 to be biased in the open position when not in use. In another embodiment (not shown), the opposing jaws may be molded separately and connected through a hinge connection that may be provided with bias means (not shown) to return the medical tool 1 in the open position when not in use. For example, the bias means may be a spring or similar types of connections.

Figure 7:
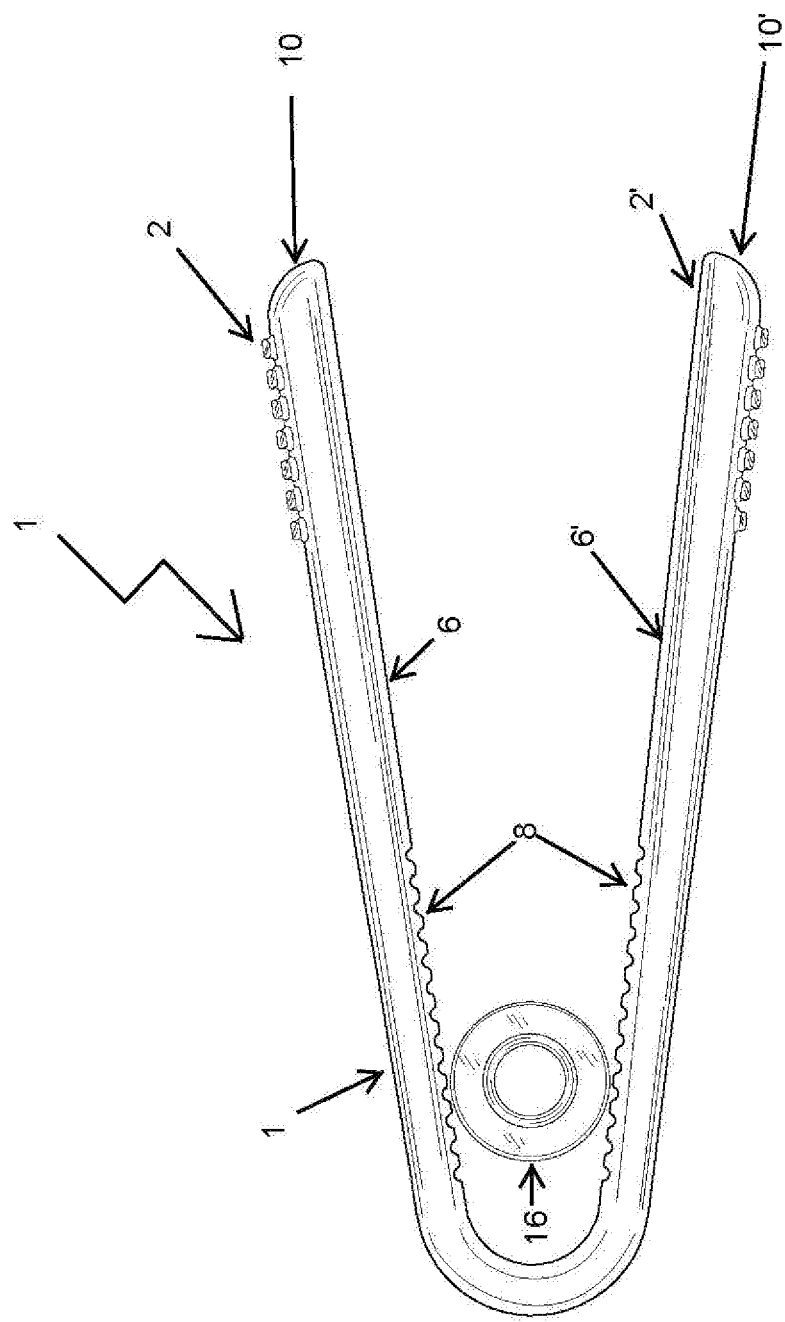
FIG. 7 is a side view of an embodiment of a medical tool in use showing medical tubing.

The medical tool 1 described above can thus be used to disconnect tight medical tubing connections, as shown in FIG. 7. A method for using the medical tool 1 may comprise inserting a medical tubing 16 between the opposing jaws 2, 2' in the open position as described above, moving the jaws 2, 2' towards each other to grip the medical tubing 16 and applying a movement, such as torsion, pulling, or the like, to provide leverage and disconnect the medical tubing connection.

Whilst the medical tool, methods and uses of the invention have been described with reference to particular embodiments, the invention is not limited to those embodiments. Further embodiments that are within or extend beyond the scope of the present description are intended to fall within the scope of the invention.

The invention claimed is:

1. A medical tool for disconnecting a connection of medical tubing, the medical tool comprising:
   a) a resilient body comprising:
      a pair of open biased opposing jaws, each of the opposing jaws defining a linear inside surface extending from a coupled end to an open end; and
      a connected end resiliently connecting the coupled end of each of the opposing jaws in an openly biased configuration, the connected end defining a U-shaped inside surface, each end of the U-shaped inside surface being coplanar with the linear inside surface of one of the jaws, the connected end having a thickness substantially similar to a thickness of the coupled end of each of the opposing jaws to enable transfer of force to at least one of the connection and the medical tubing when pressure is applied to the opposing jaws at the open end to impart movement on the connection to enable disconnection of the medical tubing from the connection; and
   b) a plurality of grooves defining gripping elements on the inside surface of the coupled end of each of the opposing jaws, the gripping elements being configured to hold at least one of the medical tubing and the connection between the opposing jaws at the coupled end without damaging the medical tubing when pressure is applied to the opposing jaws at the open end.

2. The medical tool of claim 1, further comprising friction elements on an outside surface of at least one of the opposing jaws at the open end.

3. The medical tool of claim 2 wherein the friction elements comprises raised projections or concave portions.

4. The medical tool of claim 1 made of polypropylene or rubber.

5. The medical tool of claim 1 wherein the opposing jaws are joined at the connected end by a molded connection or by a hinged connection.

6. A method for disconnecting a connection of medical tubing with a medical tool, the method comprising:
   a) inserting at least one of medical tubing and a connection in between a pair of open biased opposing jaws of a resilient body forming a medical tool, each of the opposing jaws defining a linear inside surface extending from a coupled end to an open end, the resilient body having a connected end resiliently connecting the coupled end of each of the opposing jaws in an openly biased configuration, wherein the at least one of the medical tubing and the connection are placed in contact with gripping elements defined by grooves formed in the inside surface of the coupled end of each of the opposing jaws, the gripping elements being configured to hold at least one of the medical tubing and the connection between the opposing jaws without damaging the medical tubing when pressure is applied to the opposing jaws at the open end;
   b) moving the open ends of the opposing jaws towards each other to grip at least one of the medical tubing and the connection; and
   c) imparting movement on the opposing jaws to enable disconnecting the medical tubing from the connection, wherein the connected end defines a U-shaped inside surface, each end of the U-shaped inside surface being coplanar with the linear inside surface of one of the jaws, and the connected end has a thickness substantially similar to a thickness of the coupled end of each of the opposing jaws to enable a transfer of force to at least one of the connection and the medical tubing when pressure is applied to the opposing jaws to impart movement on the connection to enable the disconnecting.

7. The method of claim 6 wherein imparting movement comprises at least one of:
   imparting a torsional movement on the opposing jaws to twist at least one of the connection and the medical tubing, and
   imparting an oppositional pulling movement on the opposing jaws and at least one of the connection and the medical tubing.

8. An apparatus comprising:
   at least one of a medical tubing and a connection for medical tubing;
   a medical tool holding the at least one of the medical tubing and the connection for medical tubing for disconnection thereof, the medical tool comprising:
   a) a resilient body comprising:
   a pair of open biased opposing jaws, each of the opposing jaws defining a linear inside surface extending from a coupled end and to an open end; and
   a connected end resiliently connecting the coupled end of each of the opposing jaws in an openly biased configuration, the connected end defining a U-shaped inside surface, each end of the U-shaped inside surface being coplanar with the linear inside surface of one of the jaws, the connected end having a thickness substantially similar to a thickness of the coupled end of each of the opposing jaws to enable transfer of force to the at least one of the medical tubing and the connection for medical tubing when pressure is applied to the opposing jaws at the open end to impart movement thereon to enable disconnection thereof; and
   b) a plurality of grooves defining gripping elements on the inside surface of the coupled end of each of the opposing jaws, the gripping elements being configured to hold the at least one of the medical tubing and the connection for medical tubing between the opposing jaws at the coupled end without damaging the medical tubing when pressure is applied to the opposing jaws at the open end.

9. The apparatus of claim 8, wherein the medical tool further comprises friction elements on an outside surface of at least one of the opposing jaws at the open end.

10. The apparatus of claim 9, wherein the friction elements comprise raised projections or concave portions.

11. The apparatus of claim 8, wherein the medical tool is made of polypropylene or rubber.

12. The apparatus of claim 8, wherein the opposing jaws are joined at the connected end by a molded connection or by a hinged connection.

* * * * *